(12) United States Patent
Golden

(10) Patent No.: US 9,687,366 B2
(45) Date of Patent: Jun. 27, 2017

(54) ENDOLEAK MITIGATOR FOR ANEURYSM STENT-GRAFT

(71) Applicant: Cordis Corporation, Fremont, CA (US)

(72) Inventor: Gerhard Johan Golden, Austin, TX (US)

(73) Assignee: Cordis Corporation, Milpitas, CA (US)

(*) Notice: Subject to any disclaimer, the term of this patent is extended or adjusted under 35 U.S.C. 154(b) by 0 days.

(21) Appl. No.: 14/744,321

(22) Filed: Jun. 19, 2015

(65) Prior Publication Data

US 2016/0367387 A1   Dec. 22, 2016

(51) Int. Cl.
*A61F 2/07*   (2013.01)
*A61F 2/856*   (2013.01)
*A61F 2/88*   (2006.01)
*A61F 2/06*   (2013.01)

(52) U.S. Cl.
CPC ............. *A61F 2/856* (2013.01); *A61F 2/07* (2013.01); *A61F 2/885* (2013.01); *A61F 2002/067* (2013.01); *A61F 2002/075* (2013.01); *A61F 2230/005* (2013.01); *A61F 2230/0069* (2013.01)

(58) Field of Classification Search
CPC ...... A61F 2/04; A61F 2/06; A61F 2/07; A61F 2/82; A61F 2/885; A61F 2/88; A61F 2/92; A61F 2/2442; A61F 2/2445; A61F 2002/065; A61F 2002/067; A61F 2002/8486
See application file for complete search history.

(56) References Cited

U.S. PATENT DOCUMENTS

| 6,458,152 B1 | 10/2002 | Khosravi et al. |
| 6,475,466 B1 | 11/2002 | Ricci et al. |
| 7,550,004 B2* | 6/2009 | Bahler ............ A61F 2/07 623/1.13 |
| 8,206,433 B2* | 6/2012 | Rucker ............ A61F 2/92 623/1.11 |
| 8,353,943 B2 | 1/2013 | Kuppurathanam et al. |
| 2004/0044396 A1 | 3/2004 | Clerc et al. |
| 2005/0266042 A1 | 12/2005 | Tseng |
| 2006/0281966 A1 | 12/2006 | Peacock |
| 2012/0191174 A1 | 7/2012 | Vinluan et al. |
| 2013/0297005 A1 | 11/2013 | Shalev |
| 2014/0052236 A1 | 2/2014 | Shalev |
| 2014/0324150 A1 | 10/2014 | Stephens et al. |

FOREIGN PATENT DOCUMENTS

| WO | 9934748 A1 | 7/1999 |
| WO | 2010027704 A1 | 3/2010 |

OTHER PUBLICATIONS

STIC search results—Jun. 1, 2016.*
Bashir, M.R., et al., "Endoleaks after Endovascular Abdominal Aortic Aneurysm Repair: Management Strategies According to CT Findings," AJR. American Journal of Roentgenology, 2009, vol. 192 (4), pp. W178-W186.
Greiner, A., et al., "The Place of Endovascular Treatment in Abdominal Aortic Aneurysm," Deutsches Arzteblatt International, 2013, vol. 110(8), pp. 119-125.

* cited by examiner

*Primary Examiner* — David Isabella
*Assistant Examiner* — Dinah Baria
(74) *Attorney, Agent, or Firm* — Khoi Q. Ta

(57) ABSTRACT

Described are various embodiments of an improved endoprosthesis with a device to mitigate or even eliminate Type I endoleaks in AAA stent-graft.

10 Claims, 4 Drawing Sheets

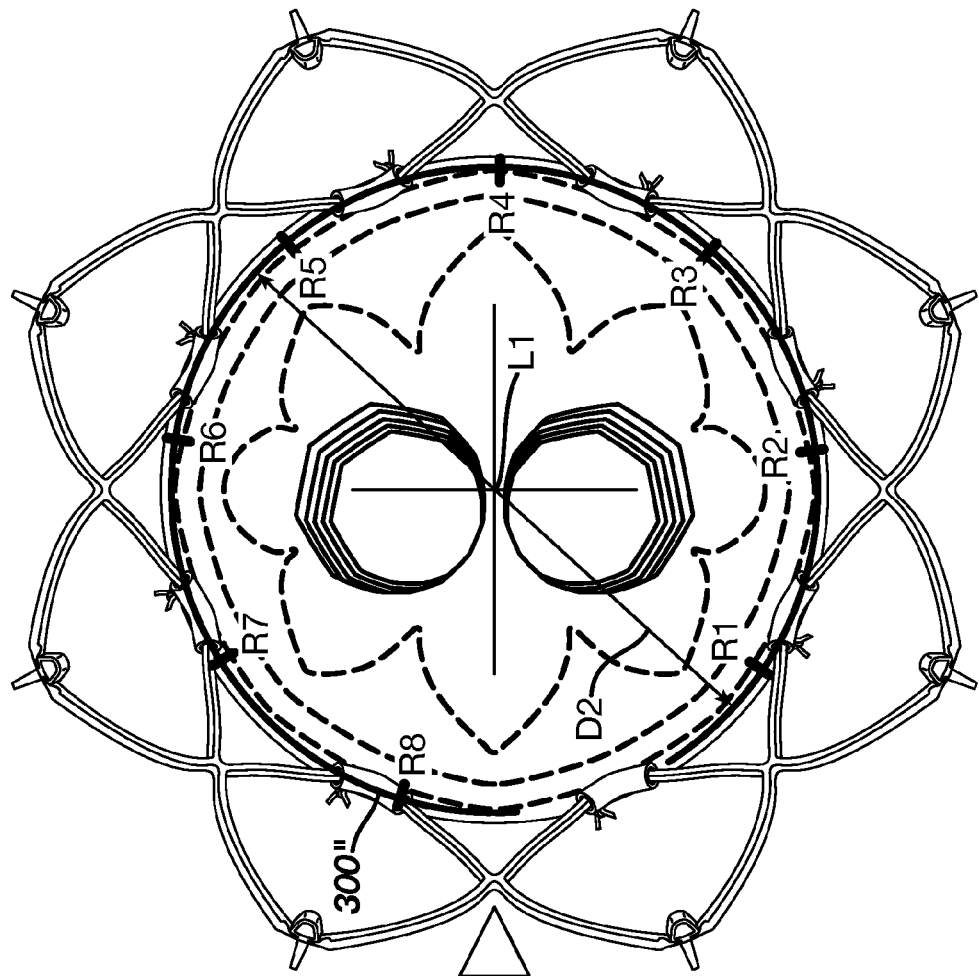
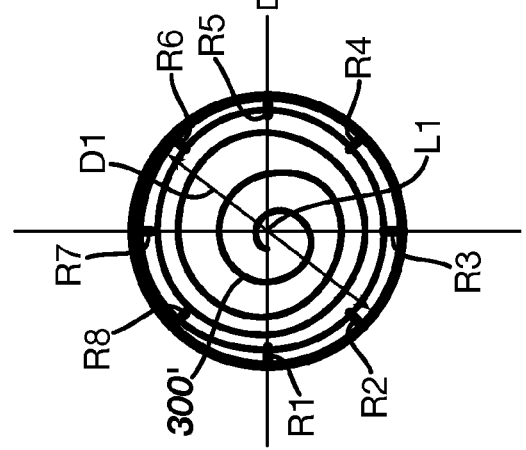

ENDOLEAK MITIGATOR FOR ANEURYSM STENT-GRAFT

BACKGROUND

An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via a transperitoneal or retroperitoneal procedure has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital and a convalescence period, at home, ranging from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed at developing less invasive, endovascular, i.e., catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now Food and Drug Administration (FDA) approved and commercially available. Their delivery procedure typically involves advanced angiographic techniques performed through vascular accesses gained via surgical cut down of a remote artery, which may include the common femoral or brachial arteries. Over a guidewire, the appropriate size introducer will be placed. The catheter and guidewire are passed through the aneurysm. Through the introducer, the stent-graft will be advanced to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3F=1 mm), arteriotomy closure typically requires open surgical repair. Some procedures may require additional surgical techniques, such as hypogastric artery embolization, vessel ligation, or surgical bypass in order to adequately treat the aneurysm or to maintain blood flow to both lower extremities. Likewise, some procedures will require additional advanced catheter directed techniques, such as angioplasty, stent placement and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome.

One concern with the use of endoprostheses is the occurrence of endo-leaks and the disruption of the normal fluid dynamics of the vasculature. One type of endo-leaks may occur where the endoprosthesis abuts against the blood vessel due to insufficient seals, also known as a Type I endo-leak. Type I endo-leak may be categorized into two sub-types: Types Ia and Ib, illustrated here in FIG. 2. Type Ia endo-leaks may occur at the junction upstream of the aneurysm (proximal to the heart) between the graft and the artery causing the aneurysm to be pressurized with blood. Type Ib can be a retrograde leak at the junction of the prosthesis and the inner artery surface downstream of the aneurysm (distal to the heart) at one or both of the branch arteries.

Type I endo-leak can occur in as many as 10% of the procedures, which will require follow up intervention within 30 days. In typical re-intervention for Type I leaks, angioplasty may be performed at the leak site(s) as well as a placement of a bare metal stent at the same location. Where the bare metal stent is not successful, additional stents can be inserted in an overlapping manner with the non-adhering portion of the prosthesis. It has been known in the field that Type Ia endo leaks can be very challenging to the point of requiring invasive open surgical repair to seal the leak using sutures or biocompatible adhesive (e.g., N-butyl-2-cyanoacrylate). It can be seen that Type I endoleaks may require a re-intervention, additional stents as well as overlapping stents and ultimately invasive open surgical repairs, which clearly defeats the advantages of the use of the minimally invasive AAA endoprosthesis.

SUMMARY OF THE DISCLOSURE

Accordingly, I have devised an improved endoprosthesis that is believed to be heretofore not available in the prior art. In particular, my improvement is an endoprosthesis for repair of aneurysms in an artery that has an arterial bifurcation for blood to flow downstream from the artery to the bifurcation. In particular, the endoprosthesis includes a main body and a leak mitigator stent frame. The main body is configured to be placed in an artery upstream of the arterial bifurcation. The main body has a cranial end with an anchor portion connected to a fabric portion of the main body. The fabric portion has inner and outer surfaces. The fabric portion is connected to a first plurality of spaced apart stent hoops. The main body extends from the distal end along a longitudinal axis into two tubular flow passages or legs, wherein each of the legs including respective second and third plurality of spaced apart stent hoops connected to the fabric portion of each leg. The leak mitigator stent frame disposed adjacent the anchor portion within an inner surface of the fabric portion such that when the leak mitigator stent frame is in an expanded configuration. The leak mitigator stent frame is disposed on an inner circumferential surface of the fabric portion about the longitudinal axis. The first portion of the leak mitigator stent frame is coupled to the fabric portion to allow circumferential movement of the leak mitigator stent frame relative to the fabric portion, the leak mitigator stent frame having a second portion uncoupled to the fabric portion so that when the leak mitigator stent frame is in an unexpanded and compressed configuration, the leak mitigator stent frame defines a spiral about the longitudinal axis while confined by the inner surface of the fabric portion.

In addition to the embodiments described above, other features recited below can be utilized in conjunction therewith to arrive at different permutations of the invention. For example, the leak mitigator stent frame may include a two side by side circumferential frame rails with a zig-zag member connected to the two side-by-side circumferential frame rails at respective apices of the zig zag member; each of the two circumferential frame rails is coupled to the fabric portion while moveable circumferentially with respect to the longitudinal axis and the fabric portion to allow the leak mitigator stent frame to expand from the spiral configuration to a fully expanded generally circular configuration; each of the two circumferential frame rails is coupled to the fabric portion via a suture configured to allow for circumferential movement of the leak mitigator stent frame relative to the fabric portion and the longitudinal axis to allow the leak mitigator stent frame to expand from the spiral configuration to a fully expanded generally circular configuration; the leak mitigator stent frame may include a shape memory material; the shape memory material may include nitinol; the device further includes suture knots extending through the graft portion to secure the spaced apart stent hoops to the graft; the spaced apart stent hoops are not connected to each other by the same material as that of each of the stent hoops; the spaced apart stent hoops are disposed on the inner surface of the graft portion; the spaced apart stent hoops are not connected to the other stent hoop by the same material of the stent hoops or the stent frame; the device further includes a first tubular extension configured for insertion into one of the two legs and a second tubular extension configured for insertion into the other of the two legs; the device further includes a leak mitigator stent frame disposed proximate an outlet of each of the tubular extensions.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF THE FIGURES

The foregoing and other features and advantages of the invention will be apparent from the following, more particular description of preferred embodiments of the invention, as illustrated in the accompanying drawings.

FIG. 5A illustrates the endoprosthesis in a first operational condition where the prosthesis is not expanded, i.e., fully compressed undeployed configuration.

FIG. 5B illustrates a top down view of FIG. 1 taken along sectioned line 5-5 where the prosthesis of FIG. 1 is fully expanded.

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. The uses of the terms "cranial" or "caudal" are in this application are used to indicate a relative position or direction with respect to the person receiving the implant. As applied to "cranial," the term indicates a position or direction closer to the heart, while the term "caudal" indicates a position or direction further away from the heart of such a subject.

Aneurysm repair devices make take on a wide variety of configurations. Aneurysm repair devices may include one element configurations or multiple element or modular element configurations. The secondary sealing mechanisms of the present invention may be utilized with many types of aneurysm repair devices that rely on a primary seal of fabric mesh against the vessel wall. While Abdominal Aortic Aneurysm (AAA) repair devices are used as specific examples, it is contemplated that this unique sealing mechanism can be used with many other types of devices at various other locations.

Figure 1:
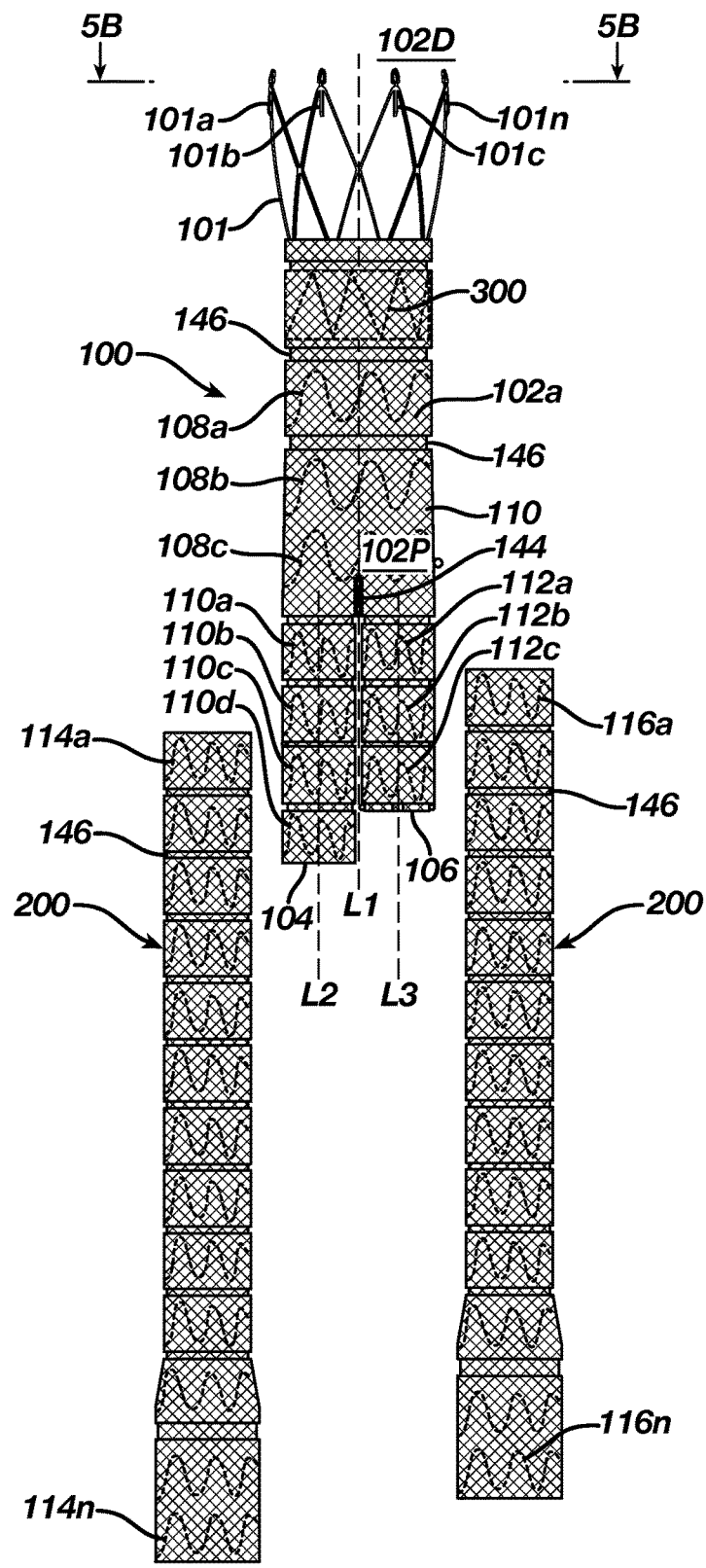
FIG. 1 illustrates the modular endoprosthesis in schematic form having a main body that bifurcates into two legs as well as respective extensions of different lengths for each of the two legs of the main body.
Figure 2:
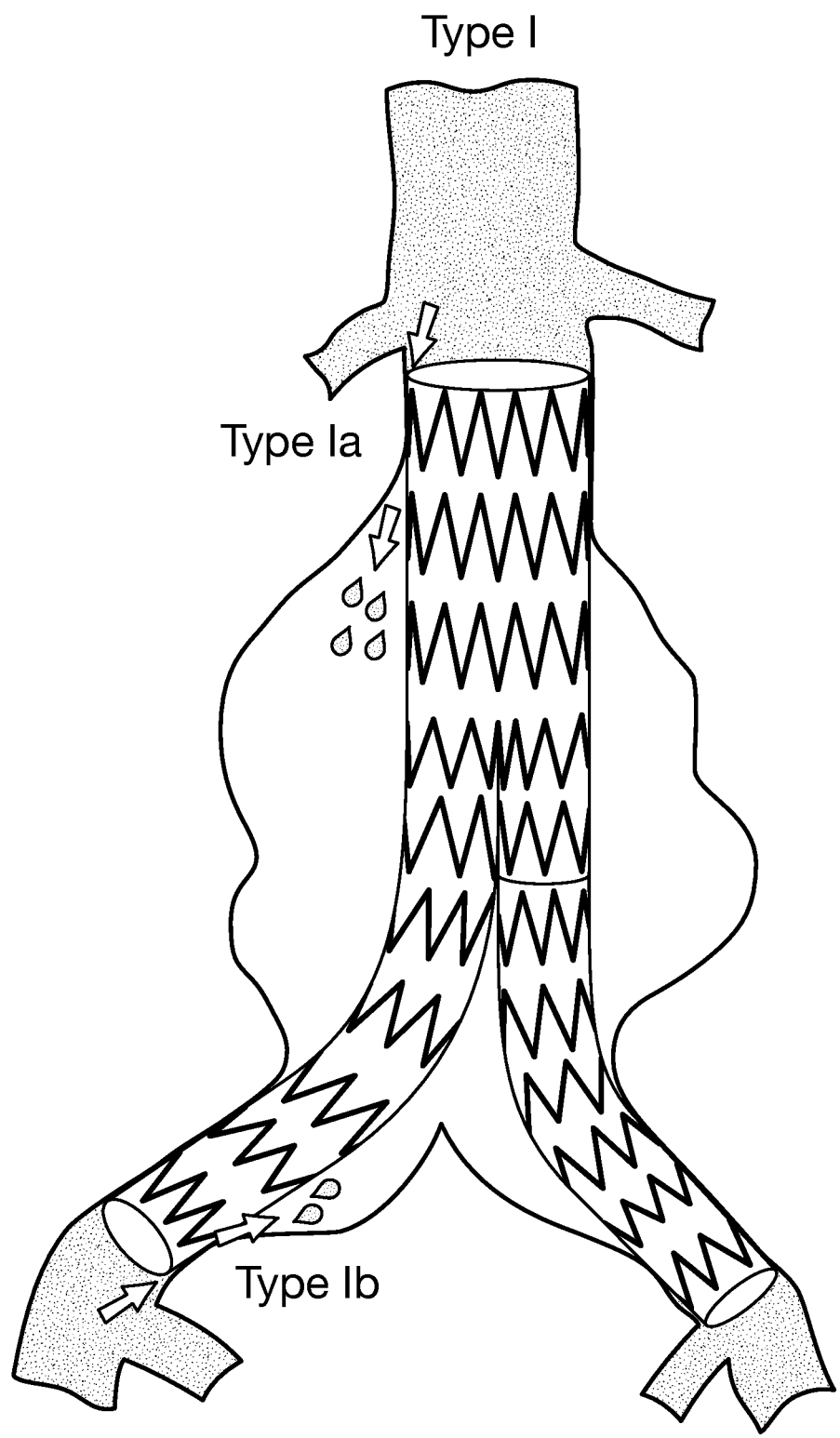
FIG. 2 illustrates the various types of endoleaks that may occur after the implantation of the endoprosthesis of FIG. 1.

Referring to FIG. 1, there is illustrated an exemplary anchoring and sealing system of a modular aneurysm repair device. The anchoring and sealing system may include a main portion 100 with two modular extensions 200 as well as a device 300 to mitigate or prevent Type I endoleaks. The main portion 100 includes trunk section 102 that extends along longitudinal axis L1 from a cranial portion 102D toward a caudal portion 102P proximate a bifurcated section, which includes two legs 104 and 106, each leg (104 or 106) defining respective longitudinal axes L2 and L3. The main body 100 has a cranial end with an anchor portion 101 connected to a fabric portion of the main body. The anchor portion 101 includes a closed diamond-like cell stent frame structure as well as barbs 101a, 101b, 101c . . . 101n disposed between the closed diamond cell to ensure that the anchor portion 101 is secured to the internal artery structure proximate the renal arteries.

The main portion 100 has a fabric material portion 102a with inner and outer surfaces, (with its outer surface indicated by cross-hatching in FIG. 1). The fabric portion 102a can be connected to a first plurality of spaced apart stent hoops 108a, 108b, 108c to a bifurcation 102P where the fabric is divided into the two legs 104 and 106. It is noted that the main body extends from the distal end 102D along a longitudinal axis L1 into two tubular flow passages or legs 104 and 106 wherein each of the legs including respective second and third plurality of spaced apart stent hoops 110a . . . 110d and 112a . . . 112c connected to the fabric portion of each leg 104 and 106. Extension members 200 can be inserted into respective legs 104 and 106. Each extension member 200 may have similar spaced-apart stent hoops 114a, 114b, 114c . . . 114n for one extension 200 (or 116a, 116b, 116c . . . 116n for the other extension 200).

Referring back to FIG. 1, the bifurcated section 102P includes two legs 104 and 106 whereby one leg, leg 104 is longer than the other leg, leg 106. This configuration eases deliverability. Each leg 104 and 106 is otherwise identical, and may include a plurality of individual, substantially tubular stent hoops 110a-110d or 112a-112c. Each stent hoop 110a-110n or 112a-112n may include a single row of struts arranged in a substantially zigzag configuration. Sutures (not labeled) are utilized to secure the graft material 110 to the stent hoops 108a-108n, 110a-110n or 112a-112n (where n=integer number). Each leg 106 and 108 is free to move independently of each other; however, proximate the junction with the trunk section 102, the graft material 110 of each leg 106 and 108 is stitched together with sutures 144. This is done to prevent tearing of the graft material 110 if and when the legs 106 and 108 move.

It is worthwhile to note that the graft material or fabric 110 covering the anchoring and sealing component 100 may include crimped sections or annular-like grooves 146 between the various underlying scaffold elements. These crimped sections 146 (in the form of a groove) increase the flexibility of the entire device. In the exemplary embodiment illustrated herein, the crimps 146 are about two mm long and 0.5 mm deep. With these dimensions, the endovascular graft can bend and flex while maintaining an open lumen. Also, prior to attachment of the graft material to the stent hoops, the graft material is cut in a shape to conform to the shapes of the stent hoops.

In use, the anchoring and sealing component 100 is percutaneously positioned in a blood vessel with one or more aneurysms. It is anchored in healthy tissue above the aneurysm and serves as the first conduit to bypass the diseased section of the artery. Additional stent-graft components or endovascular grafts 200 attach to the legs 104 and 106 to extend the bypass to healthy tissue beyond the aneurysm. The system is designed as a modular system so that as many extensions as necessary may be utilized. Essentially, the additional or modular components overlap and form an interference fit. This particular exemplary embodiment having two legs with extensions is specifically designed for branching into two vessels, for example, from the abdominal aortic artery to the iliac arteries. However, other similar modular components may be utilized in any other suitable artery.

All of the stent hoops described herein are substantially tubular elements that may be formed utilizing any number of techniques and any number of materials. In the preferred exemplary embodiment, all of the stent hoops are formed from a nickel-titanium alloy (Nitinol), shape set laser cut tubing.

The graft material utilized to cover all of the stent hoops may be made from any number of suitable biocompatible materials, including woven, knitted, sutured, extruded, or cast materials forming polyester, polytetrafluoroethylene, silicones, urethanes, and ultra-light weight polyethylene, such as that commercially available under the trade designation SPECTRA™. The materials may be porous or nonporous. Exemplary materials include a woven polyester fabric made from DACRON™ or other suitable PET-type polymers.

In one exemplary embodiment, the fabric for the graft material is a forty denier (denier is defined in grams of nine thousand meters of a filament or yarn), twenty-seven filament polyester yarn, having about seventy to one-hundred end yarns per cm per face and thirty-two to forty-six pick yarns per cm face. At this weave density, the graft material is relatively impermeable to blood flow through the wall, but is relatively thin, ranging between 0.08 and 0.12 mm in wall thickness.

The combination of the graft material and the underlying scaffold structures creates a blood carrying conduit for insertion into a vessel. The graft material may be attached to the underlying scaffold structures via any suitable means. In the exemplary embodiment set forth herein, the graft material may be attached to portions of the underlying scaffold structures by sutures. The sutures may include any suitable biocompatible material that is preferably highly durable and wear resistant. It should be noted that while these stent hoops are shown as connected to each other via the fabric and sutures (i.e., the stent hoops are not connected to each other with the same material as the material of the stent hoop itself), it is within the scope of this invention to have the spaced apart stent hoops connected to each other with the same material that makes up the stent hoop as well as via the fabric portion and suture to ensure that the stent hoops remain connected to the fabric portion.

Figure 3:
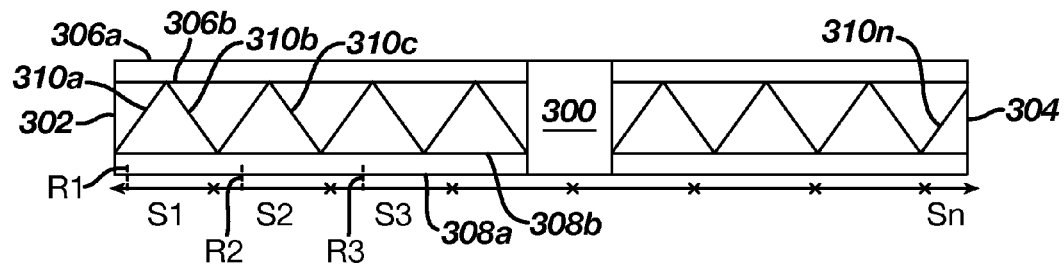
FIG. 3 illustrates the leak mitigator 300 in FIG. 1 that has been unrolled into a flat configuration for ease of illustration.

Referring back to FIG. 1, I have configured the proximal neck (i.e., upstream of the bifurcation 102P) to include a leak mitigator stent 300. In one embodiment, the leak mitigator 300 is in the form of a ladder like frame work, shown in FIG. 3 as a flattened and fully unrolled. As shown in FIG. 3, the mitigator 300 includes a first free end strut 302 and a second free end strut 304 that are free (i.e., unconnected) on one side but connected to each other via generally parallel rails 306a, 306b and 308a and 308b. That is, except for the connection via rails 306 and 308, the end strut 302 and end strut 304 are not connected when the mitigator 300 is rolled into the spiral form of FIG. 4 for attachment to the endoprosthesis 100. The mitigator 300 can be formed from a suitable biocompatible material such as, for example, self-expanding material. In one embodiment, the self-expanding material includes Nitinol. A zig-zag configuration of connectors 310a, 310b, 310c . . . 310n connect the two rails 306b and 308b to give some structural rigidity to this leak mitigator stent member 300.

Figure 4:
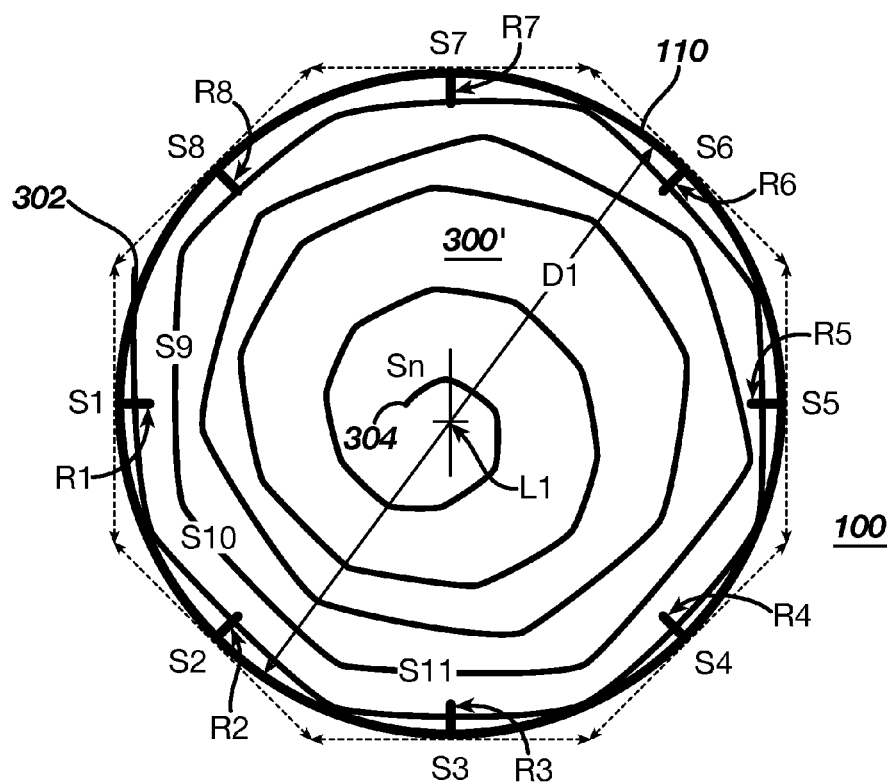
FIG. 4 illustrates a top down view of the endoprosthesis in a fully compressed undeployed condition.

Referring to FIG. 4, which is an enlarged end view of the leak mitigator 300 when it is constrained into a smaller configuration when the prosthesis 100 is unexpanded. Due to the superelastic nature of the exemplary material as well the shape memory effect of such material (in the form of Nitinol), the mitigator 300 can be conformed into the spiral configuration under a temperature lower than body temperature for crimping with the other components of the prosthesis 100. This results in a spiral configuration of the device 300 inside the fabric 110 of the prosthesis 100 as shown in the end view in FIG. 4. In particular, when the framework 300 is mounted inside the prosthesis 100, the frame work 300 is disposed about the longitudinal axis L1 whereby the frame work 300 can be folded by segments S1, S2, S3 . . . Sn so as to mimic a spiral while constrained within the circular outer circumference of the graft 110. As noted earlier, the frame work 300 in FIG. 4 may include two side by side circumferential members 306a/306b and 308a/308b connected to each other via connectors 310a, 310b, 310c . . . 310n disposed between the side by side circumferential members so that in an unexpanded and compressed configuration having a first diameter, the frame work 300 defines a spiral member 300' that extends from proximately the longitudinal axis L1 to a circumference defined by the first diameter D1 and in an expanded configuration, the frame work 300 expands to define a generally circular member 300" of a second diameter D2 greater than the first diameter D1 (FIGS. 5A and 5B). The expansion of mitigator 300 allows a circumferential force to be applied against the fabric 110 such that leaks past this junction between the fabric and artery is mitigated or even eliminated.

In FIGS. 5A and 5B, the leak mitigator 300 has been configured to operate in the following manner. In the fully compressed, undeployed configuration of FIG. 5B (as is usually in the case of a catheter sheath), the leak mitigator 300 (FIG. 3) is conformed into a spiral configuration 300' due to its pre-programmed shape memory structure. At this undeployed configuration, retainers R1-R8 (see also FIG. 4) which are in the form of suture loops, allow the rail member 306a and 308a the ability to circumferentially move with respect to the graft 100 and conform into the spiral configuration about axis L1 so as to allow the mitigator 300 to be constrained inside the smaller first diameter D1. Because the leak mitigator 300 can move with respect to the graft 100 and axis L1, when the graft 100 is allowed to expand into the larger second diameter D2, FIG. 5B, the rails 306a/306b and 308a/308b can expand into a larger circular configuration 300" whereby the rails 306 and 308 move circumferentially with respect to axis L1 during this expansion phase of the device. In other words, each of the two circumferential frame rails 306, 308 is coupled to the fabric portion 100 while moveable circumferentially with respect to the longitudinal axis L1 and the fabric portion to allow the leak mitigator stent frame 300 to expand from the spiral configuration 300' to a fully expanded generally circular configuration 300". While each of the two circumferential frame rails 306a and 308a can be coupled to the fabric portion 100 via a suture loop configured to allow for circumferential movement of the leak mitigator stent frame rails relative to the fabric portion (and the longitudinal axis L1), other retainer techniques can be utilized, such as for example, openings formed through the fabric portion so as to allow the frame rails 306a and 308a to slide or move relative thereto.

The leak mitigator 300 here is configured to have a greater outward chronic force than the other stent hoops 108a-108n of the device. The outward chronic force or the hoop force necessary to expand against a vessel by the device 300 has been selected to be at least about 0.3 Newtons per centimeter (N/cm) or higher to ensure leak mitigation or elimination. The radial resistive force of such device 300 is at least 1.6 Newtons per centimeter. In one exemplary embodiment, the outward chronic force and its counterpart, the radial resistive force (as measured using the techniques described by the paper "Physical Properties of Endovascular Stents: An Experimental Comparison" by Duda, Wiskirchen, Tepe, Bitzer, Kaulich, Stoeckel, Claussen, JVIR 11, pp. 645-654, 2000 and "Overview of Superelastic Stent Design" by Duerig, Tolomeo, Wholey, published by Min Invas Ther & Allied Technol 9(3/4) pp. 235-246, 2000, which are hereby incorporated by reference) is approximately 0.4 N/cm for the outward chronic force and approximately 1.7 N/cm for the radial resistive force.

It is noted that the free end 304 of the mitigator 300 allows the mitigator 300 to expand as much as necessary to maintain a seal. Moreover, the exemplary mitigator 300 allows conformance of the seal by the fabric 110 regardless of the pulsatile forces present in the artery that may cause leaks in the known AAA graft. In the preferred embodiments, the mitigator 300 is a material with inherent radiopacity to allow the interventional physician to determine optimal placement of the prosthesis 100 with respect to the artery vessel wall while providing an effective seal with the mitigator 300. Alternatively, radiopaque markers may also be crimped, welded or joined to the mitigator 300 to allow for visualization while the device 100 is deployed in the artery.

Although the leak mitigator 300 is shown for use proximate the neck of the main graft body, a similar leak mitigator, appropriately modified for the smaller opening, can be utilized at each of the outlet ends of the extension 200 to mitigate any retrograde leaks (i.e., Type Ib).

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. An endoprosthesis for repair of aneurysm in an artery that has an arterial bifurcation for blood to flow downstream from the artery to the bifurcation, the endoprosthesis comprising:
    a main body configured to be placed in an artery upstream of the arterial bifurcation, the main body having a cranial end with an anchor portion connected to a fabric portion of the main body, the fabric portion having inner and outer surfaces, the fabric portion being connected to a first plurality of spaced apart stent hoops, the main body extending from the cranial end along a longitudinal axis into two tubular legs wherein each of the legs including respective second and third plurality of spaced apart stent hoops coupled to the fabric portion of each leg;
    a leak mitigator stent frame disposed adjacent the anchor portion within the inner surface of the fabric portion such that when the leak mitigator stent frame is in an expanded configuration, the leak mitigator stent frame is disposed on an inner circumferential surface of the fabric portion about the longitudinal axis with a first portion of the leak mitigator stent frame coupled to the fabric portion to allow circumferential movement of the leak mitigator stent frame relative to the fabric portion, the leak mitigator stent frame having a second portion not coupled to the fabric portion so that when the leak mitigator stent frame is in an unexpanded and compressed configuration, the leak mitigator stent frame defines a spiral configuration about the longitudinal axis while confined by the inner surface of the fabric portion; and
    in which, the leak mitigator stent frame comprises two side by side circumferential frame rails with a zig-zag member connected to the two side-by-side circumferential frame rails at respective apices of the zig zag member, the two side by side circumferential frame rails are coupled to the fabric portion while moveable circumferentially will respect to the longitudinal axis to allow the leak mitigator stent to expand from the spiral configuration to a fully expanded generally circular configuration.

2. The endoprosthesis of claim 1, in which the two side by side circumferential frame rails are coupled to the fabric portion via a suture configured to allow for circumferential movement of the leak mitigator stent frame relative to the fabric portion and the longitudinal axis, and to allow the mitigator stent frame to expand from the spiral configuration to a fully expanded generally circular configuration.

3. The endoprosthesis of claim 2, further comprising a first tubular extension configured for insertion into one of the two legs and a second tubular extension configured for insertion into the other of the two legs.

4. The endoprosthesis of claim 2, in which the leak mitigator stent frame provides approximately 0.4 N/cm in an outward chronic force and approximately 1.7 N/cm for a radial resistive force.

5. The endoprosthesis of claim 1, in which the leak mitigator stent frame comprises a shape memory material.

6. The endoprosthesis of claim 5, in which the shape memory material comprises nitinol.

7. The endoprosthesis of claim 1, further comprising sutures extending through the fabric portion to secure each of the first, second, and third plurality of spaced apart stent hoops to the graft.

8. The endoprosthesis of claim 1, in which the first, second, and third plurality of spaced apart stent hoops are not connected to each other by the same material as that of each of the first, second and third plurality of stent hoops.

9. The endoprosthesis of claim 1, wherein each of the first, second, and third plurality of spaced apart stent hoops are disposed on the inner surface of the fabric portion.

10. The endoprosthesis of claim 1, in which the first, second, and third plurality of spaced apart stent hoops are not connected to each other by the same material of the first, second, or third plurality of stent hoops or the leak mitigator stent frame.

* * * * *